United States Patent [19]
Kaufman

[11] 4,304,235
[45] Dec. 8, 1981

[54] ELECTROSURGICAL ELECTRODE

[76] Inventor: John G. Kaufman, Condor Dr., Burlington, Ontario, Canada

[21] Appl. No.: 74,225

[22] Filed: Sep. 10, 1979

[30] Foreign Application Priority Data

Sep. 12, 1978 [CA] Canada .................................. 311173

[51] Int. Cl.³ ............................................ A61B 17/39
[52] U.S. Cl. ............................... 128/303.13; 128/798
[58] Field of Search ................... 128/303.13, 783, 798, 128/802, 303.14

[56] References Cited

U.S. PATENT DOCUMENTS

| | | | |
|---|---|---|---|
| 3,848,600 | 11/1974 | Patrick, Jr. et al. | 128/783 X |
| 4,117,846 | 10/1978 | Williams | 128/303.13 |
| 4,166,465 | 9/1979 | Esty et al. | 128/303.13 |
| 4,200,104 | 4/1980 | Harris | 128/303.14 |
| 4,213,463 | 7/1980 | Osenkarski | 128/303.13 X |

*Primary Examiner*—Lee S. Cohen

[57] ABSTRACT

An electrosurgical body electrode to serve as the return electrode in electrosurgical procedures, adapted to be attached to a patient's body, comprises a base cover sheet, a thin, flexible electrically-conductive metal plate adjacent the inner side of the coversheet, a thin, substantially uniform dielectric layer, e.g. polyester film, partially or completely covering the metal plate on the body attaching side, along with adhesive sections for releasably attaching the electrode to the patient's body skin and an electrical connector for connecting the metal plate into an electrical circuit. The electrode causes capacitive coupling of the body into the electrical circuit, for return of the high frequency electric current used in electrosurgical procedures. The cover sheet is stretchable, to press the metal plate into contact with the body of the patient, and includes a stretch indicator to show the operative that the plate is in proper contact under the stretched cover sheet.

3 Claims, 8 Drawing Figures

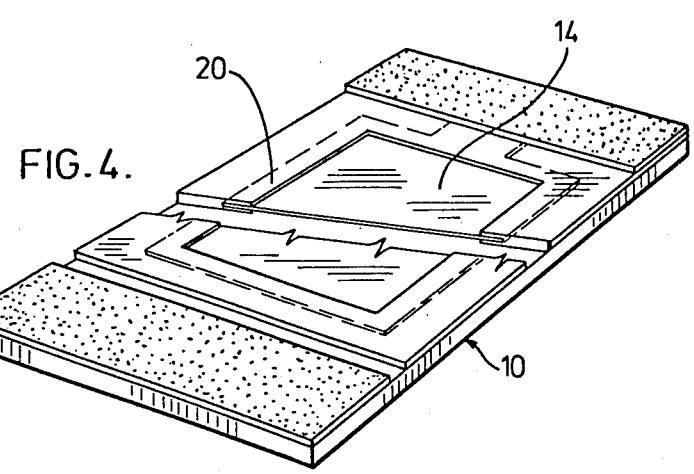
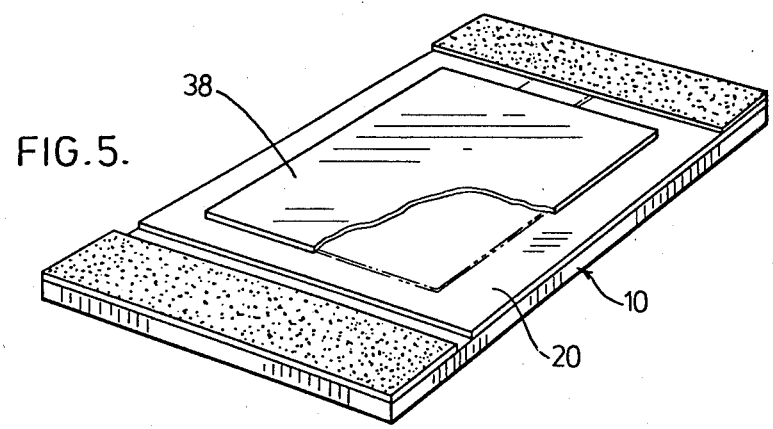
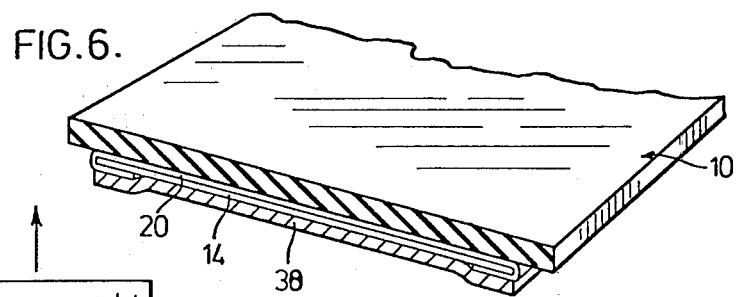
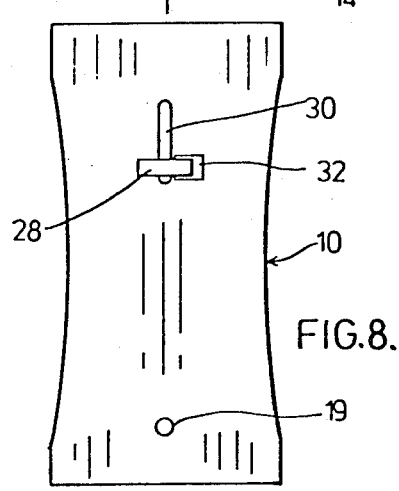
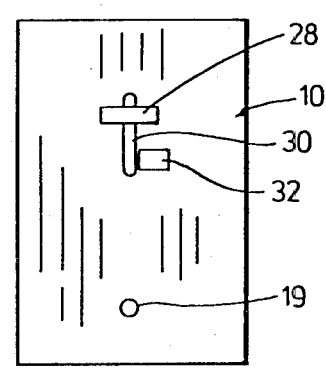

ELECTROSURGICAL ELECTRODE

This invention relates to electrosurgical equipment, and more particularly to a return electrode for attachment to a patient's body, to serve as part of the electrical circuit during electrosurgical operations.

Such a body electrode has to be capable of conducting the very sizable currents employed in electrosurgical procedures away from the patent's body, without causing severe damage to the patient's skin. Very high frequency electrical currents, of substantial magnitude (e.g 500 watts of power) are used, in order that the electronic scalpel can make suitable cuts to tissue without causing significant amounts of bleeding. The requirements for an electrosurgical body electrode are therefore quite different from those of a monitoring body electrode, such as those used in electro-cardiograms, where detection and monitoring of extremely small currents is required.

Since an electrosurgical body electrode has to handle currents of large magnitude, it is necessary that it have a substantial current conducting surface area presented to the patent's body. Small surface areas lead to large current densities and hence to risk of causing skin burns to the patient. Not only should the body electrode have substantial conductive surface area, but also the full extent of the conductive surface area should be utilized, substantially evenly, to avoid the development of "hot spots" and consequent burning of the patient's skin. Moreover, the resistance or impedance of the body electrode should be low, so that excessive amounts of electric power do not have to be introduced into the electrical circuit in order to obtain the necessary cutting action of the scalpel.

Previously proposed electrosurgical body electrodes have included a conductive metal plate, of substantial surface area, which in use is separated from the patent's skin by a skin-contacting layer of, for example, textile or other porous material. The skin contacting layer is wetted with a conductive gel, liquid or paste to render it electrically conductive. Reliance is then placed on the creation of a direct current electrical conductive path through the gel. This presents practical problems. If the conductive material is applied to the layer when the electrode is manufactured and sold, there is a risk that it will deteriorate or dry out during storage, and become insufficiently conductive. If the electrode is packaged dry, so that the conductive medium must be applied to a skin contacting layer at the time of application of the electrode to the patient, there is a risk of operator error. Electrosurgical procedures are frequently carried out under emergency conditions, so that minimizing the risks of inoperative electrodes and operator error in application of them under stress is important.

The present invention provides an electrosurgical body electrode in which the need for application of conductive medium such as gel, paste or liquids is reduced or even eliminated. It has been found that, in accordance with the present invention, a dielectric layer, substantially non-conductive of direct electric current, can be satisfactorily used between the patient's skin and the conductive metal plate of the electrode. On account of the fact that electrosurgical procedures employ alternating currents of very high frequency, dielectric separation of the plate from the body can be utilized, to cause capacitive coupling between the patient's body and hence conduct the current safely away from the body.

A dielectric layer is thus placed on the patient's skin when the body electrode is in place, and separates the metal plate of the electrode from the skin. In use, the skin and the metal plate act as if they were capacitor plates, with the dielectric material as the central capacitor dielectric and effecting capacitive coupling of the "plates".

In one embodiment of electrode according to the invention, the dielectric layer comprises a layer of non-conductive adhesive material, such as pressure sensitive adhesive material, completely covering the second major surface of the conducting metal plate, and useful also for adhesive attachment of the electrode to the body. Thus the dielectric may be a semisolid pressure sensitive adhesive composition, applied by brushing or rolling onto the metal plate surface, and protected until ready for use by a peelable release film. Alternatively and more preferably, the dielectric layer is a continuous film of a thermoplastic material, for example a stretchable polyester film such as Mylar, provided with adhesive coating on both its surfaces, so that it will adhere both to the body skin and to the metal plate when in use. As a further alternative, the dielectric layer may be adhesive on its surface presented away from the patient's body only, so that other means such as differently located adhesive sections are used for body attachment.

In a second embodiment, the base cover sheet has a larger area than that of the flexible conductive metal plate, the latter being positioned perimetrically within the surface area of the base cover sheet, and a second dielectric sheet in the form of a mask is provided. The dielectric mask comprises an apertured sheet, overlying both the base cover sheet and the second major surface of the flexible conductive metal plate, with the aperture therein exposing a major portion of the second major surface of the metal plate. The thin, substantially uniform dielectric layer then comprises a layer of dielectric adhesive material, e.g. adhesive coated plastic film, and overlies both the dielectric mask surface and the exposed portion of the metal plate surface. In such an arrangement, the dielectric constant of the mask is higher than that of the substantially uniform layer. As a result, capacitive coupling is effected in use through the metal-adhesive coated area, whilst at the same time extra protection is afforded to the patient's skin at the edge areas of the electrode plate. In this case also, the substantially uniform layer of dielectric may be adhesive on both sides, so that it is utilized for body attachment purposes, or on its metal plate adjacent surface so that alternative means are used for body attachment.

In the third embodiment of the present invention, the electrically conductive metal plate is totally or partially covered on its major surfaces with dielectric plastic film, e.g. by lamination or encapsulation. Such electrodes are simple and economical to manufacture on a continuous basis, e.g. by feeding pre-cut metal plates continuously into contact with sheets of plastic film such as polyester, on one or both major surfaces as desired, and heat sealing of the plastic. In one alternative of this third embodiment, the metal plate electrode is totally encapsulated in an envelope of thermoplastic film such as polyester. The film thickness on the body presented surface may be thicker than that on the other surface. The film layer overlying the body presented surface of the metal plate constitutes the aforesaid substantially uniform dielectric layer overlying the second major surface of the conductive plate. The electrode in such case is best attached to the body by adhesive sections disposed away from the second major surface of the conductive plate, e.g. on the cover sheet beyond the edges of the conductive plate. In another alternative of this embodiment, the substantially uniform dielectric layer overlies only the perimetric portion of the conductive metal plate, thereby providing in use for direct metal-skin contact in the central area of the electrode. Capacitive coupling is thus provided over a portion of the surface area only, and direct electrical contact is arranged over the remaining portion of the surface area.

A fourth embodiment of the present invention also provides for a combination of capacitive coupling and direct electrical coupling over different areas of the surface of the body electrode. In this embodiment, there is provided a conductive metal plate with a dielectric plastic film completely covering the first major surface of the metal plate, i.e. the surface presented away from the body and towards the cover sheet, and either completely or partially, in the perimetric area, covering the second major surface area thereof, and a layer of resiliently compressible substantially non-absorbent foam material provided on the second major surface overlying the dielectric plastic film. In use, a conductive gel or cream is applied to the foam to contact the body, so that the electrode uses a combination of capacitive and direct electrical coupling to complete the operating circuit.

It has been found that there are practical advantages to the use of capacitively coupled body electrode pads, in addition to their simplicity of structure and application, and in addition to their economy of manufacture. When direct electrical coupling is utilized, e.g. by application of electrically conductive creams, gels and the like between the body and the metal plate electrode, the current will flow by the path of least resistance. Unless therefore substantially constant, even thickness of gel or cream layer is maintained, the current will flow unevenly over the surface area of the plate, with the risk of causing hot spots and burns to the patient. The current shows a particular affinity to concentrate at the edge of the plate. When capacitive coupling is employed, however, substantially uniform current density over the whole area of the electrode plate ("capacitor plate") is achieved automatically, and variations in pressure of different areas of the plate surface against the body are more easily tolerated.

The base cover sheet is suitably of electrically insulating material, and totally covers the metal plate surface. It can desirably be of resiliently stretchable material such as foam rubber polyurethane, with the metal plate secured to it at one location only, or, at other location, loosely and flexibly attached only. Then, in embodiments of the invention where the electrode is attached to the body by means of spaced apart adhesive sections of the cover sheet, the metal plate and dielectric cover thereof remaining unsecured to the body, the electrode can be applied to the patient's body with the cover sheet in a resiliently stretched condition. On a convex body contour such as an arm or a leg, the cover sheet presses and holds the plate in close proximity to the body. In such an embodiment, the present invention provides a means for indicating that the cover sheet of the electrode has been applied to the patient's body in a properly stretched condition to press and hold the plate in close proximity thereto. Such a stretch indicator is suitably a visible registration means on the surface of the cover sheet presented away from the patient's body during use of the electrode, so that an operator or attendant can observe that the electrode remains properly attached during a surgical procedure. Such a visible registration means may comprise an item on the plate extending through or visible through an elongated aperture in the cover sheet, said aperture being elongated in the general direction of stretch of the cover sheet. The position of the item in the aperture, e.g. its registry with indicia on the cover sheet outer surface, will indicate the stretch or otherwise of the cover sheet.

Typically, the metal plate is generally rectangular in shape, having a surface area of from about 4 to about 25 square inches. The plate is flexible so that it may conform to body contours on application. It is suitably of aluminum or stainless steel. The dielectric layer, when provided as a mask or continuous layer, may be for example of non-conductive dielectric plastic such as polyethylene, polypropylene, polyester (esp. Mylar), polyamide, polyvinyl chloride, etc., or of cellulose (textile or paper), rubber or the like. Suitably its thickness is in the range 1/1000 to 1/100 inch. In any of the above embodiments, it is advantageous to provide an extra layer of dielectric, underlying the electrical connection means, to provide further protection against patient burns in that vicinity.

Body electrodes according to the invention can be used dry, eliminating the need for application of gels, creams, pastes or liquids to provide a conductive path, saline pads or the like. It is thus simple to manufacture, package and apply, and avoids the risk of drying out during storage, or during prolonged surgical operations.

Specific embodiments of the invention are illustrated in the accompanying drawings, in which:

FIG. 4 is a view similar to FIG. 1 of a variation of the third embodiment shown in FIG. 3;

FIG. 5 is a view similar to FIG. 1 of a fourth embodiment of the invention;

FIG. 6 is a view similar to FIG. 1 of a variation of the fourth embodiment shown in FIG. 5;

FIG. 7 is a top plan view of one form of a body electrode according to the present invention, in a relaxed condition;

FIG. 8 is a view similar to that of FIG. 7 but with the body electrode in a stretched, applied condition.

Figure 1:
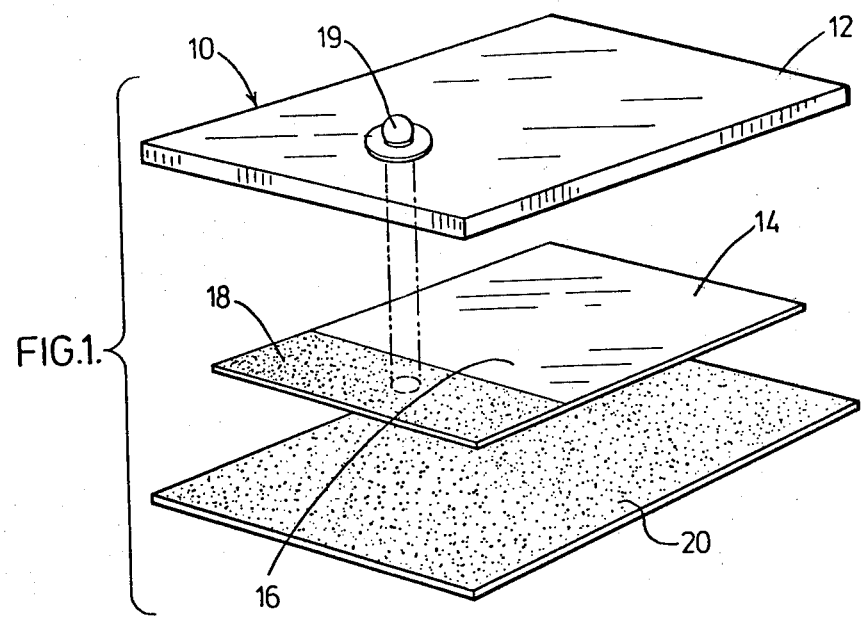
FIG. 1 is an exploded perspective diagrammatic view of a first embodiment of a body electrode according to the invention.

With reference to FIG. 1 of the accompanying drawings, there is illustrated a body electrode according to a first embodiment of the invention, and comprising a resiliently stretchable insulating cover sheet 10 of soft foam polyurethane, having an outer major surface 12 which in use is presented away from the patient's skin. A thin flexible metal plate 14, of stainless steel or aluminum or other suitable electrically conductive metal, is located with its first, major, outer surface 16 against the inner major surface of the cover sheet 10. It is adhesively secured to the cover sheet 10 adjacent one end by a layer of adhesive 18. In the area of adhesive 18, the plate 14 has an integral electrical connection means, namely a dot fastener 19, protruding from its outer surface 16, and through the cover sheet 10 to be exposed for electrical connection above the outer major surface 12 thereof. Below the plate 14 and in contact with a lower second major surface thereof, is a layer of dielectric adhesive material 20. In the embodiment illustrated the dielectric 20 is a continuous film of polyester of substantially uniform thickness about 3/1000 of an inch, and designated by the trade mark MYLAR, and provided with a pressure sensitive non-conductive adhesive on both sides thereof, so as to arrange for adhesion of the assembly to the patient's body during use, and to complete the assembly itself, with the perimetric portions of the adhesive on the upwardly presented major surface of the film 20 adhering to the cover sheet 10. The film 20 overlies the whole of the lower major surface area of plate 14, at all sides thereof.

In alternatives to the illustrated form of this embodiment, the MYLAR layer 20 may be provided with adhesive on its upper surface only, and adhered to the metal plate 14 but not to the cover sheet 10. Then, the sole connection of the cover sheet 20 is by means of adhesive attachments 18 and dot fastener 19, and the connection to the patient's body is by means of separate and distinct adhesive sections, one at each end of the cover sheet. Thus, the plate 14 and dielectric layer 20 are left free for movement relative to the cover sheet 10 over the major portion of their surface area, and the cover sheet 10 can be applied to the patient's body in a resiliently stretched condition to press the electrode against the patient's body by means of its resilient retractive force.

In another alternative as illustrated in FIG. 1, sheet 20 may represent a layer of dielectric pressure sensitive adhesive. In such event, exposed adhesive surfaces and surface sections are covered with peelable release papers until ready for application to the patient's body. In this embodiment, the electrode is applied to the patient's body without the use of electrically conductive gels, creams, pastes and the like, and relies solely on capacitive coupling to complete the electrical circuit.

Figure 2:
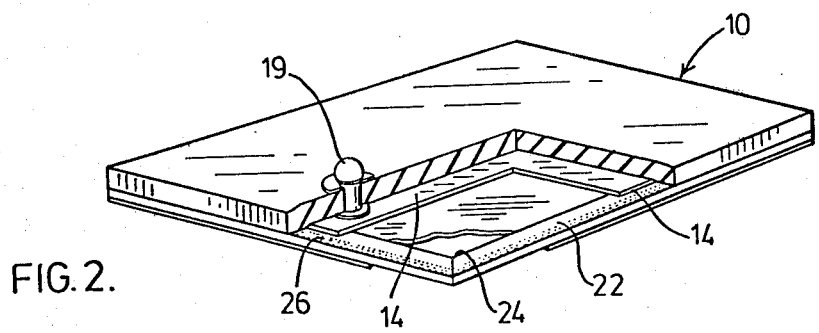
FIG. 2 is a view similar to FIG. 1 of a second embodiment of a body electrode according to the invention.

The embodiment as shown in FIG. 2 is essentially the same as that of FIG. 1, except that there is additionally provided a dielectric mask 22, between the metal plate 14 and the dielectric layer 20 of film or adhesive. The mask 22 overlies the perimetric portion of the plate 14, but is apertured at 24 to expose the major portion of the surface of the plate 14. Outwardly of the perimeter of the metal plate 14, the mask 22 is adhered to the cover sheet 10 by means of adhesive 26 extending all the way around the edge of rubber pad 10. However, metal plate 14 is not adhered to either mask 22 or cover pad 10, and is secured to pad 10 only in the vicinity of the dot fastener 19. The metal plate 14 thus has a degree of freedom of movement with respect to both cover sheet 10 and mask 22, over the major portion of its surface area. Then the assembly can be applied in a resiliently stretched condition, as mentioned in connection with the previous embodiment, to press the plate 14 against the dielectric layers and enhance the uniformity of the distance of the plate from the patient's skin over its area.

The lower surface of the assembly, i.e. the surface which is presented to the patient's body in use, is coated with a layer of non conductive dielectric adhesive over substantially the entire surface area, i.e. over the surface of mask 22 and metal plate 14. This is a layer of biocompatible pressure sensitive adhesive, for attachment of the assembly to the patient's skin. The mask 22 is of a dielectric material which has a lower dielectric constant than that of the plastic film 20. Paper is a suitable material, especially opaque paper, to improve appearance of the assembly. The presence of the dielectric mask 22 provides extra protection for the patient against edge effects of the plate 14. This embodiment of the invention is used without application of conductive gels, creams or the like. It is an extremely economical pad to manufacture, relying wholly on capacitive coupling and thereby creating a circuit of increased impedance. It therefore requires increased power in the circuit. The natural tendency at the high frequency electric current to concentrate at the plate edges, with consequent risk of burn to the patient at such locations, is effectively counteracted by the provision of the dielectric buffer or mask, reducing the current flow from the edges.

Figure 3:
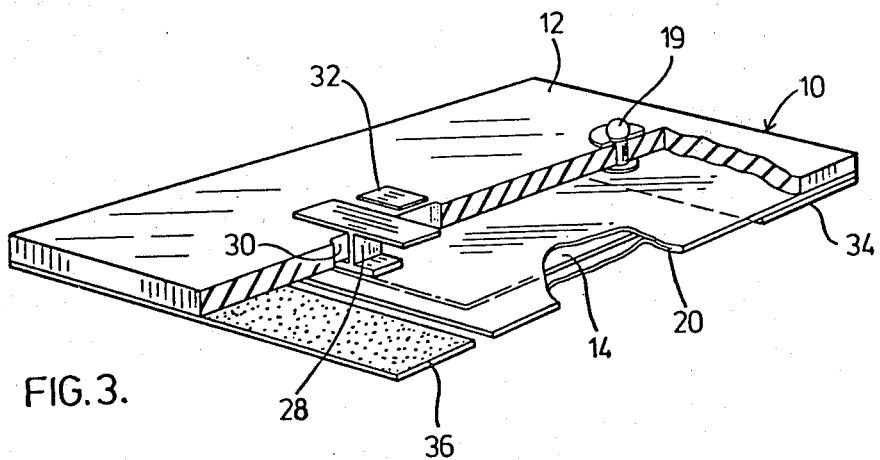
FIG. 3 is a view similar to FIG. 1 of a third embodiment of a body electrode according to the invention.

In the embodiments shown in FIGS. 3 and 4, the dielectric layer 20 comprises polyester film (MYLAR) laminated to the plate 14. In FIG. 3, the plate 14 is wholly encapsulated in MYLAR, which thereby covers both major surfaces. The dot connector 19 protrudes from the plate 14 through the MYLAR film and onto the top surface 12 of the cover sheet 10 as before. At the other end of the metal plate 14 there is provided a protruding T-bar 28 which protrudes through an elongated slit aperture 30, in the cover sheet 10, to be visible on the top surface 12 thereof. Indicia 32 are marked alongside an end of the slit 30 on cover sheet surface 12 to register with T-bar 28 and provide an indication of stretch of the cover sheet 10 with respect to the metal plate 14. This is more clearly shown in FIGS. 7 and 8. Otherwise the cover sheet 10 and the metal plate 14 and film 20 are unattached to each other, so that the plate 14 has a degree of freedom with respect to the sheet 10 and can be pressed into contact with the patient's skin by resilient relaxation of the sheet 10. Lubrication, e.g. by means of powdered talc or the like, is provided between the coversheet 10 and the upper layer of MYLAR, to enhance this freedom of movement. An adhesive section 36 is provided on one end of the cover sheet 10, on the bottom surface thereof, and an adhesive 34, spaced from section 36, is provided on the bottom surface of film 20, at the opposed end, for attachment of the assembly to the patient's body. The embodiment of FIG. 4 is essentially the same as that shown in FIG. 3, with the exception that the film 20 only partially covers the lower, body presented surface of the metal plate 14, leaving a rectangular aperture to expose the centre part of the metal. In this case, direct skin-metal contact is employed, the dielectric film 20 providing protection to the patient's skin against edge effects. The rectangular cut-out in the dielectric film, to allow direct metal body contact, reduces the impedance in the circuit by about 15% and permits use of lower power ranges in the electrical circuits.

A fourth embodiment of the invention is shown in two variations, in FIGS. 5 and 6. As compared with the assemblies of FIGS. 3 and 4 respectively, these include layers of open cell foam rubber material 38, on the bottom-most surface, to contact the patient's body, overlying the underside of both the metal plate 14 and the MYLAR film 20. In these arrangements, conductive cream or gel is applied to the foam rubber 38, and is held against flow but not absorbed thereby. The assembly is then applied to the patient's body by means of adhesive sections 34, 36, optionally with the cover sheet 10 in a stretched condition. Then the patient gets the benefit of a combination of capacitive and direct electrical coupling and connection. In the form shown in FIG. 5, the metal plate is protected from the corrosive effects of the gel, enabling a cheaper metal to be used for the metal plate, e.g. aluminum as opposed to stainless steel. In the form shown in FIG. 6, the edge protection previously described has been embodied, together with the reduced power requirement by use of a "frame" of dielectric. The pre-gelled foam enhances the coupling to the body.

In yet another embodiment of the invention, having the appearance of that shown in FIG. 1 of the accompanying drawings, adhesive layer 20 represents a layer of electrically conducting adhesive, for example a resin-based pressure sensitive adhesive with conductive metal particles dispersed therein. Such an embodiment provides for a combination of direct current electric coupling and capacitive coupling of the plate to the patient's body, and can be used in replacement of known, gelled surface pack.

FIGS. 7 and 8 show in more detail the arrangement of stretch indicator which can be provided on any of the above embodiments in which the cover sheet 10 can be stretched with respect to the metal plate 14, and be applied to the patient's body in such relatively stretched condition to apply a retractive force thereon against the patient's body surface. The cover sheet 10 is provided, at its end remote from dot connector 19, with an elongated slit aperture 30 extending in the longitudinal direction. At its end nearest the connector 19, the slit is bounded by visually distinctive indicia 32, e.g. a differently coloured area. The T-bar 28 protrudes from the metal plate 14 through aperture 30, with the T-ends thereof extending transversely to the extent of the slit. When the cover sheet is not stressed as shown in FIG. 7, the T-bar ends are located away from the indicia 32. When the cover sheet 10 is stretched with respect to the metal plate 14, the T-bar ends register with the indicia 32. Thus in cases where the assembly is applied to the patient in a stretched condition of cover sheet 10, and the resilient relaxation force of the sheet 10 is being relied upon to make the necessary electrical contact, the operator can quickly observe visually whether the assembly has been correctly applied and whether it is remaining in the correctly stressed condition during the course of the operation. In body electrodes of this type, it is extremely important that the coversheet remain stretched relative to the metal plate, throughout the duration of the operation whilst it is applied to the patient's body. The stretch indicator according to the invention allows instantaneous observation of the stretched condition by the operator, at any time during the conduct of the operation, so that detection of a potential burn situation can be made promptly, to allow rapid correction.

The T-bar serves the additional function of providing a loose, flexible attachment of the plate to the cover sheet, to better hold the assembly together without interfering with relative free movement between the parts. An alternative stretch indicator comprises a mark on the plate visible through the slit aperture 30, to register with indicia on the cover sheet. In such arrangement it is best to include a rubber resilient loose connecting strip between the unsecured ends of the plate and cover sheet for better maintenance of the assembly.

It has been described above that a pad relying on or utilizing direct coupling to provide the return path for high frequency current in electrosurgery may suffer from edge effects. The current passes preferentially through the edges of the plate, leading to risk of edge burns. When sole reliance is placed upon capacitive coupling, more even dispersion of current is achieved, and edge effects are substantially eliminated. In many pads, however, the absence of perfect conducting materials and perfect dielectric materials results in the use of a mixture of capacitive coupling and direct coupling. Another embodiment of the invention comprises an electrode plate and cover sheet as described, the body-presented side of the plate having deposited thereon a plurality of discrete areas of non-conducting dielectric layer. The said side may also be provided with an edge mask of dielectric material as described, laminated thereto. Then a layer of foam material to receive conductive cream or gel, may be provided to contact the body. Such an arrangement effectively provides a metal plate electrode having a large number of edges of conductive area, to promote the even dispersion of current passing by a direct coupling mechanism.

The performance of embodiments of the body electrodes according to the present invention were evaluated in specific experiments, as follows:

An electrode under test was affixed to the thigh of a patient. A reference electrode was affixed to the same leg of the patient, above the ankle. The reference electrode served as input for current from a Valley Lab SSEII generator, while the electrode under test served as the return electrode. An RF ammeter was used to measure current flow at various settings of power of the generator. In the experiments, the current was set in cutting mode, and the output was increased in steps of 0.5 settings on the dial of the instrument. A current reading was taken at each setting, and the patient's perception was noted at each setting. The generator was turned on for 20 seconds by the patient, and a forty second interval was allowed between successive readings. A ten minute interval was allowed between successive electrode testing. The patient could turn the generator off at any time before the end of 20 seconds, if there was a sensation or possibility of a burn. This did not happen throughout the experiments.

The current measured by the RF ammeter in the circuit indicates, inter alia, the resistance or impedance of the electrode under test. In practice, the surgeon turns up the setting of the generator until he obtains a satisfactory current level at the electronic scalpel for proper cutting action during surgery. The greater the resistance or impedance of the return electrode, the greater the amount of power needed in the generator circuit to the scalpel, and the higher the setting of the generator machine which must be used. Uses of excessive power in the circuit should be avoided.

As reference electrode, there was used a stretchable gelled body electrode as described and illustrated in Canadian Pat. No. 1,032,227 John G. Kaufman, issued May 30, 1978, this is a commercially available pad which is well accepted and widely used in practice. In a control experiment, this form of pad was used as both electrodes of the circuit. The surface plate area of these reference electrodes was 67 square centimeters.

The experimental pads according to the invention, which were tested in this manner, were as follows:

(a) a pad according to the fourth embodiment of the invention and as illustrated in FIG. 6, with a conductive gel applied to the foam rubber layer, metal plate area 94 square centimeters;

(b) a body electrode according to the third embodiment of the invention, and as illustrated in FIG. 3 of the accompanying drawings, the encapsulating film 20 being of MYLAR of thickness 3/1000 of an inch on both sides of the metal plate, metal plate electrode area 74 square centimeters;

(c) a body electrode according to the third embodiment of the invention and as illustrated in FIG. 3, the thickness of MYLAR on the body contacting side being 1.5/1000 of an inch, and the thickness of MYLAR on the upper side of the metal plate being 3/1000 of an inch, metal plate electrode area 74 square centimeters;

(d) a body electrode according to the third embodiment of the invention and as shown in FIG. 4 of the accompanying drawings, with electrode plate area 129 square centimeters and an electrode area exposed and touching the patient's body of 75 square centimeters;

(e) an electrode as in the case of electrode (c), but with surface area 128 square centimeters;

(f) an electrode according to the fourth embodiment of the invention and as illustrated in FIG. 5, with conductive gel applied to the lower foam rubber layer in contact with the patient's body, electrode plate area 99 square centimeters and plastic dielectric film thickness 15/1000 inch.

The current drawn by all seven electrodes was of the same order of magnitude at corresponding generator settings. The current drawn by electrode (b) was the smallest of all, but the feeling of warmth experienced by the patient was also less for this electrode. Electrodes (d) and (e) were similar to each other and similar the reference electrode in current drawing capacity. Electrode (a) was the most efficient in drawing current. In general, all of the electrodes have similar characteristics and have an efficiency within 15 percent of the accepted reference electrode.

The scope of the invention is limited only by the scope of the appended claims.

What is claimed is:

1. An electrosurgical body electrode comprising:
a resiliently stretchable base cover sheet having a first, outer surface and a second, inner surface;
a thin, flexible, electrically conductive metal plate having its first major surface disposed adjacent the inner surface of said base cover sheet, and its second major surface disposed away therefrom, said metal plate having a degree of free movement relative to said cover sheet;
a thin, substantially uniform, dielectric layer overlying the entire first major surface and the perimetric edge portion only of the second major surface of said conductive metal plate;
first and second spaced apart, discrete adhesive sections provided, respectively, on the inner surface of said cover sheet and on said dielectric layer located on the second major surface of said conductive metal plate for releasably attaching said electrode to a patient's body skin with the second major surface of the conductive metal plate presented towards the patient's body and the first major surface thereof presented away from the patient's body, with said cover sheet in an elastically stretched condition;
electrical connection means electrically connected to said conductive metal plate and accessible for electrical connection when the body electrode is secured to a patient's body;
a stretch indicator comprising an item on said metal plate visible from the outer surface of said cover sheet and indicia on the outer surface of said cover sheet and movable therewith on resilient stretching of the cover sheet, said item and said indicia being put into visible predetermined registry with one another when the cover sheet is correctly resiliently stretched.

2. The electrode of claim 1 further including a layer of resiliently compressible substantially non-absorbent foam material overlying at least a portion of the dielectric layer and the second major surface of the metal plate, said foam layer adapted to be wetted with conductive gel and presented to contact the body surface in use.

3. The electrode of claim 1 wherein the stretch indicator comprises a protrusion attached to the metal plate and protruding through an elongated slit aperture in the cover sheet to be visible against the outer surface of the cover sheet when the electrode is applied to the patient's body, the position of said indicator in the slit aperture relative to the indicia on the outer surface of said cover sheet indicating the stretch of the cover sheet relative to the metal plate.

* * * * *